US006482841B1

United States Patent
Letelier et al.

(10) Patent No.: US 6,482,841 B1
(45) Date of Patent: Nov. 19, 2002

(54) PYRIDYL COMPOUNDS AND PHARMACEUTICAL COMPOSITIONS CONTAINING THEM

(75) Inventors: Carlos Sunkel Letelier, Madrid (ES); Miguel Fau De Casa-Juana Munoz, Madrid (ES); Julio Alvarez-Builla Gomez, Madrid (ES); José M. Minguez Ortega, Madrid (ES); Pierre Statkow, Geneva (CH); Danielle Straumann, Martigny (CH); Shyam S. Chatterjee, Karlsruhe (DE)

(73) Assignee: Cermol S.A., Evionnaz (CH)

( * ) Notice: Subject to any disclaimer, the term of this patent is extended or adjusted under 35 U.S.C. 154(b) by 0 days.

(21) Appl. No.: 09/529,112

(22) PCT Filed: Oct. 7, 1998

(86) PCT No.: PCT/IB98/01555
§ 371 (c)(1),
(2), (4) Date: Apr. 7, 2000

(87) PCT Pub. No.: WO99/19302
PCT Pub. Date: Apr. 22, 1999

(30) Foreign Application Priority Data

Oct. 9, 1997 (CH) .............................................. 2364/97

(51) Int. Cl.$^7$ ..................... C07D 213/63; A61K 31/435
(52) U.S. Cl. ........................ 514/354; 514/355; 546/314; 546/315
(58) Field of Search ................................ 514/277, 354, 514/355; 546/250, 251, 314, 315

(56) References Cited

U.S. PATENT DOCUMENTS 4,497,821 A * 2/1985 Wehinger et al. ............ 514/302
4,698,350 A * 10/1987 Daum et al. ................. 514/312

FOREIGN PATENT DOCUMENTS

| DE | 44 30 639 A1 | 3/1996 |
| EP | 179239 | * 4/1986 |
| EP | 0 297 613 A2 | 1/1989 |
| EP | 0 387 070 A2 | 9/1990 |
| EP | 0 551 663 A1 | 7/1993 |
| EP | 0 636 611 A2 | 2/1995 |
| WO | 97/27177 | * 7/1997 |

OTHER PUBLICATIONS

Caplus 116:106096 (English Abstract of JP 03223253) formula II and III and RN 138994–28–2, Oct. 1991.*
USPATFULL 87:69997 (Abstract US 4698350) Daum et al RN # 104431–76–7, Oct. 1987.*
Caplus 115:247746 English Abstract, Mol. Pharmacol Oct. 1991 40(3) pp. 435–439.*
"The merck index, 11$^{th}$ edition" 1989, Merck & Co., Inc., Rahway, N.J. USA, XP002088691, citation 6441. Nifedipine, pp. 1031, col. 2, and pp. 1032, col. 1.
V.S. Goldmann et al., "1,4–Dihydrophyridine: Einfluss von Chiralität und Konformation auf die Calcium–antogonistische und agonistische Wirkung," Angawandte Chemie, vol. 103, No. 7, 1991, pp. 1587–1665.

* cited by examiner

Primary Examiner—Alan L. Rotman
Assistant Examiner—Rita Desai
(74) Attorney, Agent, or Firm—Young & Thompson

(57) ABSTRACT

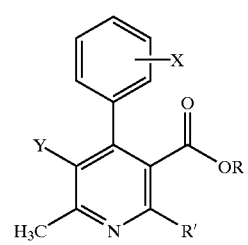

The present invention is concerned with new pyridine double esters of formula (I), their acids, and pharmaceutically acceptable salts. These compounds can be obtained by oxydation of the corresponding 1,4-dihydropyridines, and they are useful as cardioprotective agents in pharmaceutical compositions.

6 Claims, No Drawings

PYRIDYL COMPOUNDS AND PHARMACEUTICAL COMPOSITIONS CONTAINING THEM

The present invention relates to a series of new pyridine derivatives, their preparation procedures, their use as cardioprotective agents, and the pharmaceutical compositions containing said derivatives. More particularly, the object of the present invention is constituted by pyridine derivatives of general formula (I), in which

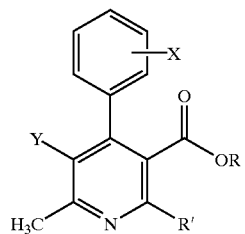

(I)

X represents H, $NO_2$, OH, CN, F, Br, Cl, $CF_3$, —NH—CO—$CH_3$, 2,3-$Cl_2$, 2,3-$(OCH_3)_2$, 4-Cl, 3-$NO_2$ and 2-[CH=CH—COO—C$(CH_3)_3$], and the fused cycle 2,3-oxadiazole [2,3-(=N—O—N=)];

Y represents an alcoxycarbonyl fragment $R^3$OOC—, where $R^2$ can be H, a small alkyl group, 2-methoxyethyl, 2-tetrahydrofurfuryl or 5,5-dimethyl-1,3,2-dioxaphosphorinan-2-yl;

R represents H, an small alkyl group or, alternatively, the following fragments: 2-methoxyethyl, 2-(benzyl-methylamino)ethyl, 2-tetrahydrofurfuryl, 5-oxotetrahydrofurfuryl, 3-[(4,4-diphenyl)-piperidinyl]propyl, (R)-1-benzyl-3-piperidinyl, 2-(N-benzyl-(N-phenylamino)ethyl, (S)-1-benzyl-3-pirrolidinyl, 2-[(4-diphenylmethyl)-1-piperazinylethyl, 3-phenyl-2-propenyl, dually-amino-alkyl, 2-(N-morpholino)ethyl or 1,3-di(N-morpholino)isopropyl R' represents $CH_3$, CN or —$CH_2$—O—$(CH_2)_2$—$NH_2$, as well as the corresponding optical isomers, and the pharmaceutically acceptable salts of the said compounds.

As non-limiting examples, the following compounds corresponding to formula (1) of the present invention can be mentioned:

4-(2,3-Dichloro-phenyl)-2,6-dimethyl-pyridine-3, 5-dicarboxylic acid 3-methyl ester 5-(tetrahydrofuran-2-ylmethyl) ester 2,6-Dimethyl-4-(3-fluorophenyl) pyridine-3, 5-dicarboxylic acid 3-methyl ester 5-(tetrahydrofuran-2-ylmethyl) ester 4-(3-Acetylaminophenyl)-2,6-dimethyl pyridine-3, 5-dicarboxylic acid 3-methyl ester 5-(tetrahydrofuran-2-ylmethyl) ester (hydrochloride)

2,6-Dimethyl-4-(3-hydroxyphenyl) pyridine-3, 5-dicarboxylic acid 3-methyl ester 5-(tetrahydrofuran-2-ylmethyl) ester (hydrochloride)

2,6-Dimethyl-4-phenyl-pyridine-3, 5-dicarboxylic acid 3-methyl ester 5—(tetrahydrofuran-2-ylmethyl) ester 2,6-Dimethyl-4-(3-nitrophenyl)-pyridine-3, 5-dicarboxylic acid 3,5-di(tetrahydrofuran-2-ylmethyl) ester (hydrochloride)

4-(3-Cyanophenyl)-2,6-dimethyl pyridine-3, 5-dicarboxylic acid 3-methyl ester 5-(tetrahydrofuran-2-ylmethyl) ester 2,6-Dimethyl-4-(3-nitrophenyl) pyridine-3, 5-dicarboxylic acid 3-methyl ester 5-(tetrahydrofuran-2-ylmethyl) ester 2,6-Dimethyl-4-(2-nitrophenyl) pyridine-3, 5-dicarboxylic acid 3-methyl ester 5-(tetrahydrofuran-2-ylmethyl) ester 4-(4-Chloro-3-nitrophenyl)-2,6-dimethyl pyridine-3, 5-dicarboxylic acid 3-methyl ester 5-(tetrahydrofuran-2-ylmethyl) ester 4-(3-Bromophenyl)-2,6-dimethyl pyridine-3, 5-dicarboxylic acid 3,5-di(tetrahydrofuran-2-ylmethyl) ester 2,6-Dimethyl-4-(3-trifluoromethylphenyl) pyridine-3, 5-dicarboxylic acid 3-methyl ester 5-(tetrahydrofuran-2-ylmethyl) ester 4-(2-Chlorophenyl)-2,6-dimethyl pyridine-3, 5-dicarboxylic acid 3-methyl ester 5-(tetrahydrofuran)-2-ylmethyl) ester 2,6-Dimethyl-4-(2-trifluoromethylphenyl) pyridine-3, 5-dicarboxylic acid 3-methyl ester 5-(tetrahydrofuran-2-ylmethyl) ester 2,6-Dimethyl-4-(2,3-dimethoxyphenyl) pyridine-3, 5-dicarboxylic acid 3-methyl ester 5-(tetrahydrofuran-2-ylmethyl) ester 4-(3-Chlorophenyl)-2,6-dimethyl pyridine-3, 5-dicarboxylic acid 3-methyl ester 5-(tetrahydrofuran-2-ylmethyl) ester 2,6-Dimethyl-4-(2-nitrophenyl) pyridine-3, 5-dicarboxylic acid 3-methyl ester 5-(5-oxotetrahydrofuran-2-ylmethyl) ester (S)-2,6-Dimethyl-4-(2-nitrophenyl) pyridine-3, 5-dicarboxylic acid 3-methyl ester 5-(tetrahydrofuran-2-ylmethyl) ester (R)-2,6-Dimethyl-4-(2-nitrophenyl) pyridine-3, 5-dicarboxylic acid 3-methyl ester 5-(tetrahydrofuran-2-ylmethyl) ester 4-(2-Bromophenyl)-2,6-dimethyl pyridine-3, 5-dicarboxylic acid 3-methyl ester 5-(tetrahydrofuran-2-ylmethyl) ester 2,6-Dimethyl-4-(3-nitrophenyl)-pyridine-3, 5-dicarboxylic acid 3-isopropyl ester 5-(2-methoxyethyl) ester 2,6-Dimethyl-4-(2-nitrophenyl)-pyridine-3, 5-dicarboxylic acid 3-methyl ester 5-isobutyl ester 2,6-Dimethyl-4-(3-nitrophenyl) pyridine-3, 5-dicarboxylic acid 3-ethyl ester 5-methyl ester 2,6-Dimethyl-4-(2-nitrophenyl) pyridine-3, 5-dicarboxylic acid dimethyl ester 4-[2-(2-tert-Butoxycarbonylvinyl)-phenyl]-2,6-dimethyl pyridine-3, 5-dicarboxylic acid diethyl ester 2,6-Dimethyl-4-(3-nitrophenyl) pyridine-3, 5-dicarboxylic acid 3-methyl ester 5-(N-methylbenzylamino)ethyl ester 4-(2,3-Dichlorophenyl)-2,6-dimethyl pyridine-3, 5-dicarboxylic acid 3-ethyl ester 5-methyl ester 2,6-Dimethyl-4-(2-nitrophenyl) pyridine-3, 5-dicarboxylic acid 3-methyl ester 2,6-Dimethyl-4-(2-nitrophenyl) pyridine-3, 5-dicarboxylic acid 2-(2-Aminoethoxy)methyl-4-(2-chlorophlnyl)-6-methyl pyridine-3, 5-dicarboxylic acid 3-ethyl ester 5-methyl ester 2,6-Dimethyl-4-(3-nitrophenyl) pyridine-3, 5-dicarboxylic acid 3-(2-methoxyethyl) ester 5-(3-phenyl)propen-2-yl ester 2,6-Dimethyl-4-(2-nitrophenyl) pyridine-3, 5-dicarboxylic acid 3-(2-dimethylaminoethyl) ester 5-methyl ester (dihydrobromide)

2,6-Dimethyl-4-(2-nitrophenyl) pyridine-3, 5-dicarboxylic acid 3-(2-diethylaminoethyl) ester 5-methyl ester (dihydrochloride)

2,6-Dimethyl-4-phenylpyridine-3, 5-dicarboxylic acid dimethyl ester 2,6-Dimethyl-4-(2-nitrophenyl) pyridine-3, 5-dicarboxylic acid 3-(3-dimethylaminopropyl) 5-methyl ester (dihydrochloride).

2,6-Dimethyl-4-(2-nitrophenyl) pyridine-3, 5-dicarboxylic acid 3-methyl ester 5-(N-morpholino)ethyl ester (dihydrochloride)

2,6-Dimethyl-4-(2-nitrophenyl)pyridine-3,5-dicarboxylic acid 3-methyl ester 5-[1,3-di(N-morpholine)isopropyl] ester trihydrochloride The compounds corresponding to formula (Ia, examples 1–30) could, in a general method, be prepared by oxydation of 1,4-dihydropyridines corresponding to formula (II). In some cases, when X=2—NO$_2$, many dihydropyridines II could be rather unstable, so products had to be obtained through Ib and III, (Scheme I), allowing the preparation of new derivatives Ic. In the scheme, X, R and R' are like have been defined before, and R", although differentiated for clarity in the scheme, should be taken as defined for R.

This can facilitate the preparation of galenic forms requiring the administration of the product dissolved in water.

The mixtures of diastereomers or enantiomers can be separated using the differences of physico-chemical properties of the products, through the usual methods as fractional crystallisation, chromatography, reactions with asymmetric induction, or by the action of enzymes or micro-organisms.

The present inventors had put in evidence the fact that the pyridine compounds with formula (I), according the present invention, have a cardioprotective activity and thus, can be used as cardioprotective agents. In addition, another object of the present invention consists in pharmaceutical prepa- Scheme I

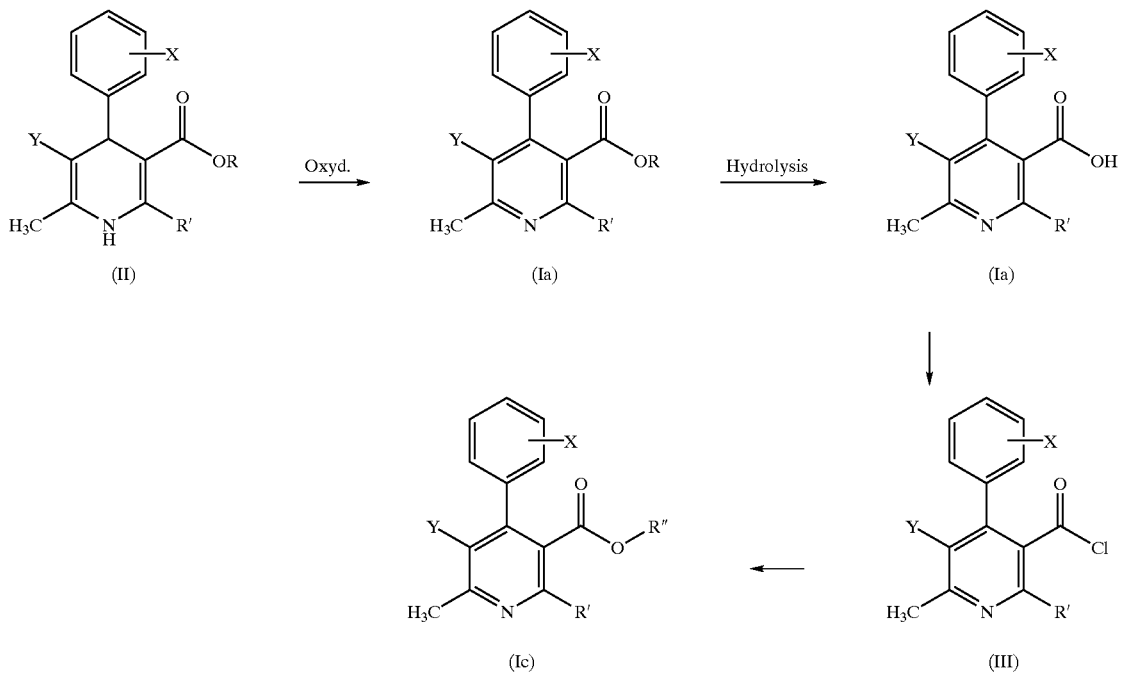

The 1,4-dihydropyridine derivatives (II) are either already known, or could be prepared by the standard procedures described in the literature.

As oxydation agents for preparation of the compounds (a) it is possible to use all described for standard oxydation procedures, as oxygen, NaNO$_2$/NOAc, NaNO$_2$/HCl, HNO$_3$, Fe(NO$_3$)$_3$ or Cu(NO$_3$)$_2$, Br$_2$+NaAcO, CrO$_3$, sulphur, KMnO$_4$, chloranyl or o-chloranyl, 2,3-dihydro-5, 6-dicyano-1,4-benzoquinone (DDQ), Pd/C, pyridinium chlorochromate adsorbed on alumina (PCC/Al$_2$O$_3$), pyridinium dichromate, MnO$_2$, etc. Controlled ester hydrolysis of Ia, to produce Ib, activation through III and esterification to Ic are described in the present report.

The pharmaceutically acceptable salts obtained by addition of acid to the compounds (I) are prepared by conventional methods, by treatment of a solution or suspension of the free base (I) with one or two equivalents of a pharmaceutically acceptable acid, either organic or inorganic. To give some examples, it is possible to mention the following acids: hydrochloric, hydrobromic, sulphuric, phosphoric, acetic, citric, oxalic, malonic, salicylic, malic, lactic, p-toluenesulphonic, gluconic, fumaric, succinic, ascorbic, maleic, methanesulphonic and benzenesulphonic. The obtained salts can show some advantages, particularly in relation with higher solubility in polar solvents as water.

rations containing at least, one compound of formula (I), as previously defined, or one of its pharmaceutically acceptable salts.

The compounds of formula (I) according the invention can be administered alone but, in general, they would be administered as a mixture with a selected pharmaceutical excipient, depending of thr route of administration and the standard pharmaceutical practice. As an example, they can be administered by oral route, either in the form of tablets, containing excipients as starch or lactose, or in capsules, either alone or mixed with excipients, or in the form of syrups or suspensions, containing colour or aromatic substances. They can also be injected by parental route, as by example, by intramuscular, intravenous or subcutaneous route. When administered by parenteral route, they will be preferably used in the form of sterile aqueous solution, which can contain other solutes, as for instance, salt or glucose, to render the solution isotonic.

The pharmaceutical compositions according the invention could contain a quantity of any of the products with general formula (I) in the way the level of the administered dose being between 0.01 and 20 mg/kg. The daily dose of the active principle depends of the administration route. In general, an oral dose between 5 and 1000 mg/day will be used.

While when administered intramuscular route, the product can be given in one dose or divided up to three doses, when intravenously administered the product can be included into a dropwise system, for continuous supply. There will be necessarily variations depending of the weight and conditions of the patient, as well as of the administration route chosen.

In that way, the pharmaceutical compositions according the present invention, can be used as new drugs for the prevention or treatment of cardiovascular diseases, as cardiomyopaties, myocardium infarction, angina, cardiac failures, coronary vasospasm, valvular heart disease, etc.

The present invention will be illustrated in reference to some examples of preparation of compounds according the invention, as well as the results of the tests of toxicity and pharmacological activity.

Example 1

2,6-Dimethyl-4-phenyl pyridine-3,5-dicarboxylic acid dimethyl ester

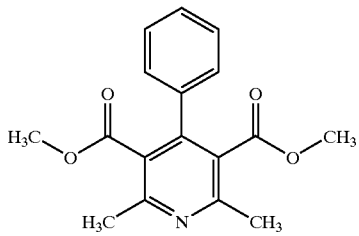

Over a suspension of 119 g (0.1 mol) of pyridinium chlorochromate absorbed on alumina in 330 ml of $CH_2Cl_2$, 10 g (0.033 mol) of 2,6-dimethyl-4-phenyl-1,4-dihydropyridine-3,5-dicarboxylic acid dimethyl ester were portionwise added with stirring. The mixture was maintained with stirring at room temperature for 8 hours. The remaining solid was eliminated by filtration, and the liquid was washed with water (3×500 ml), dried over anh. $Na_2SO_4$, and concentrated at reduced pressure, to dryness. The product was obtained as a solid, (mp 133–5° C., MeOH) with a yield of 75%.

Analysis Calculated for $C_{17}H_{17}NO_4$

|  | % C | % H | % N |
|---|---|---|---|
| Calc. | 68.22 | 5.72 | 4.68 |
| Obs. | 68.09 | 5.63 | 4.64 |

Example 2

2,6-Dimethyl-4-phenyl-pyridine-3,5-dicarboxylic acid 3-methyl ester 5-(tetrahydrofuran-2-ylmethyl) ester

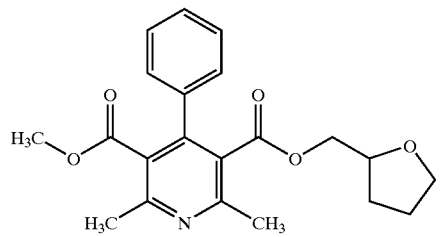

A) 2,6-Dimethyl-4-phenyl-1,4-dihydropyridine-3,5-dicarboxylic acid 3-methyl ester 5-(tetrahydrofuran-2-ylmethyl) ester A solution of 20 g (0.10 mol) of methyl benzylideneacetoacetate and 18.14 g (0.10 mol) of (tetrahydrofuran-2-ylmethyl)-3-aminocrotonate in 100 ml of 2-propanol was refluxed with stirring along 24 hours. The solvent was evaporated at reduced pressure, and the residue obtained was crystallised in 15 ml of diisopropylether. A white solid was obtained (mp 117–9° C., diisopropylether) with a yield of 82%.

B) 2,6-Dimethyl-4-phenyl-pyridine-3,5-dicarboxylic acid 3-methyl ester 5-(tetrahydrofuran-2-ylmethyl) ester A mixture of 8 g (0.022 mol) of 2,6-dimethyl-4-phenyl-1,4-dihydropyridine-3,5-dicarboxylic acid 3-methyl ester 5-(tetrahydrofuran-2-ylmethyl) ester, obtained as described in A), and 2.15 g (0.025 mol) of $MnO_2$ suspended in 15 ml of methylisobutylketone was refluxed with stirring along 14 hours. The remaining solid was filtered of, and the solution obtained was concentrated at reduced pressure. The residue obtained was then dissolved in 15 ml of aq HCl 5%, washed with EtAcO (20 ml), and the aqueous phase was taken to pH 8 with aq $K_2CO_3$ 20%. Then, the aqueous phase was extracted with EtAcO (2×50 ml) and the organic extracts were dried (anh. $Na_2SO_4$) and concentrated to dryness under vacuum. An oil was obtained, which crystallised in diisopropylether (2 ml), producing a white solid (45–7° C., diisopropylether) with a yield of 59%.

Analysis Calculated for $C_{21}H_{23}NO_5$.

|  | % C | % H | % N |
|---|---|---|---|
| Calc. | 68.28 | 6.28 | 3.79 |
| Obs. | 68.03 | 6.26 | 3.85 |

Example 3

2,6-Dimethyl-4-(3-fluorophenyl) pyridine-3,5-dicarboxylic acid 3-methyl ester 5-(tetrahydrofuran-2-ylmethyl) ester

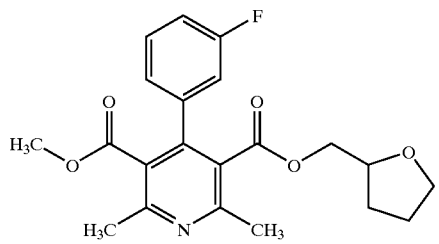

A) 2,6-Dimethyl-4-(3-fluorophenyl) 1,4-dihydropyridine-3,5-dicarboxylic acid 3-methyl ester 5-(tetrahydrofuran-2-ylmethyl) ester A solution of 25 g (0.11 mol) of methyl 3-fluorobenzylideneacetoacetate and 20.84 g (0.11 mol) de (tetrahydrofuran-2-ylmethyl)-3-aminocrotonate in 110 ml of abs. ethanol was refluxed with stirring for 8 hours. Then, the solvent was evaporated under vacuum, up to 60 ml and the mixture was cooled to −10° C.; a precipitate was obtained and on filtration, the product was obtained as a clear yellow solid, with a m.p. of 118–20° C.(EtOH), and with a yield of 88%.

B) 2,6-Dimethyl-4-(3-fluorophenyl) pyridine-3,5-dicarboxylic acid 3-methyl ester 5-(tetrahydrofuran-2-ylmethyl) ester To a solution of 8 g (0.021 mol) of 2,6-dimethyl-4-(3-fluorophenyl) 1,4-dihydropyridine-3,5-dicarboxylic acid 3-methyl ester 5-(tetrahydrofuran-2-ylmethyl) ester, (obtained as indicated before) in 20 ml of acetic acid, and with stirring, 2.06 g (0.21 mol) of $CrO_3$ were slowly added, with stirring. Once the addition was complete, reflux with stirring was maintained for one hour. Then, the reaction mixture was cooled at room temperature and added to a mixture of 50 ml $NH_4OH$ and ice. The resulting solution was then extracted with $CH_2Cl_2$ (3×100 ml), and the organic extracts were washed with water (250 ml) and dried with anh. $Na_2SO_4$. Finally, the solvent was evaporated at reduced pressure, and an oil was obtained which crystallised with 5 ml of pentane. The product was obtained as a white solid, of m.p. 66–8° C. (EtOH), with a yield of 65%.

Analysis Calculated for $C_{21}H_{22}NFO_5$

|  | % C | % H | % N |
|---|---|---|---|
| Calc. | 65.11 | 5.72 | 3.62 |
| Obs. | 65.23 | 5.95 | 3.45 |

Example 4

4-(2-Chlorophenyl)-2,6-dimethyl pyridine-3,5-dicarboxylic acid 3-methyl ester 5-(tetrahydrofuran-2-ylmethyl) ester

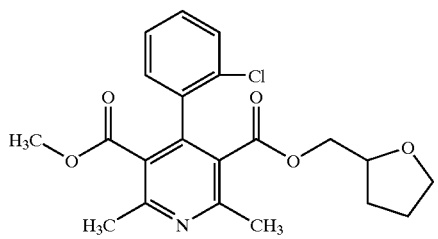

A) 4-(2-Chlorophenyl)-2,6-dimethyl-1,4-dihydropyridine-3,5-dicarboxylic acid 3-methyl ester 5-(tetrahydrofuran-2-ylmethyl) ester A solution of 15 g (0.06 mol) of methyl 2-chlorobenzylideneacetoacetate and 11.64 g (0.06 mol) of (tetrahydrofuran-2-ylmethyl)-3-aminocrotonate in 65 ml of abs ethanol, was refluxed with stirring in the absence of light, along 18 hours. Then 30 ml of solvent were evaporated, and the remaining solution was cooled to −10° C. In that way, a yellow solid was obtained (mp 165–7° C., EtOH) with a yield of 86%.

B) 4-(2-Chlorophenyl)-2,6-dimethyl pyridine-3,5-dicarboxylic acid 3-methyl ester 5-(tetrahydrofuran-2-ylmethyl) ester A mixture of 8 g (0.02 mol) of 4-(2-chlorophenyl)-2,6-dimethyl-1,4-dihydropyridine-3,5-dicarboxylic acid 3-methyl ester 5-(tetrahydrofuran-2-ylmethyl) ester, obtained according A) and 71 g (0.059 mol) of pyridinium chlorochromate adsorbed on alumina, was suspended in 200 ml of $CH_2Cl_2$, and the whole mixture was stirred at room temperature for 5 hours. The remaining solid was eliminated by filtration, and the liquid was washed with water (3×250 ml), dried over anh. $Na_2SO_4$, and concentrated at reduced pressure, to dryness. The product was obtained as an oil, which was purified by column chromatography (Silicagel, n-hexane:EtAcO, 8:2) with a yield of 66%, Analysis Calculated for $C_{21}H_{22}ClNO_5$

|  | % C | % H | % N |
|---|---|---|---|
| Calc. | 62.46 | 5.49 | 3.47 |
| Obs. | 62.43 | 5.57 | 3.59 |

Example 5

4-(3-Chlorophenyl)-2,6-dimethyl pyridine-3,5-dicarboxylic acid 3-methyl ester 5-(tetrahydrofuran-2-ylmethyl) ester

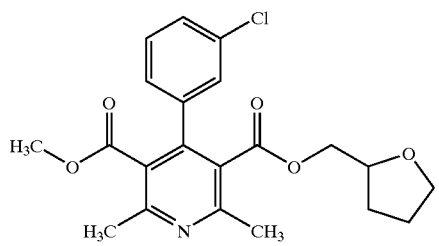

A) 4-(3-Chlorophenyl)-2,6-dimethyl-1,4-dihydropyridine-3,5-dicarboxylic acid 3-methyl ester 5-(tetrahydrofuran-2-ylmethyl) ester A solution of 15 g (0.06 mol) of methyl 3-chlorobenzylideneacetoacetate and 11.64 g (0.06 mol) of (tetrahydrofuran-2-ylmethyl)-3-aminocrotonate in 65 ml of abs. ethanol, was refluxed with stirring and in the absence of light, for 8 hours. Then, the reaction mixture was cooled to −10° C. and a white solid precipitated (137–9° C., MeOH) with a yield of 87%.

B) 4-(3-Chlorophenyl)-2,6-dimethyl pyridine-3,5-dicarboxylic acid 3-methyl ester 5-(tetrahydrofuran-2-ylmethyl) ester A mixture of 8 g (0.02 mol) de 4-(3-chlorophenyl)-2,6-dimethyl-1,4-dihydropyridine-3,5-dicarboxylic acid 3-methyl ester 5-(tetrahydrofuran-2-ylmethyl) ester, obtained according A), and 71 g (0.059 mol) of pyridinium chlorochromate absorbed on alumina, was suspended in 200 ml of $CH_2Cl_2$. Then, the whole mixture was maintained with stirring at room temperature, along 8 hours. The remaining solid was eliminated by filtration, and the liquid was washed with water (3×250 ml). dried over anh. $Na_2SO_4$, and concentrated at reduced pressure, to dryness. The product was obtained as an oil, which was purified by column chromatography (Silicagel, n-hexane:EtAcO, 8:2) with a yield of 70%.

Analysis Calculated for $C_{21}H_{22}ClNO_5$

|  | % C | % H | % N |
|---|---|---|---|
| Calc. | 62.46 | 5.49 | 3.47 |
| Obs. | 62.40 | 5.68 | 3.30 |

Example 6

4-(2,3-Dichlorophenyl)-2,6-dimethyl pyridine-3,5-dicarboxylic acid 3-methyl ester 5-(tetrahydrofuran-2-ylmethyl) ester

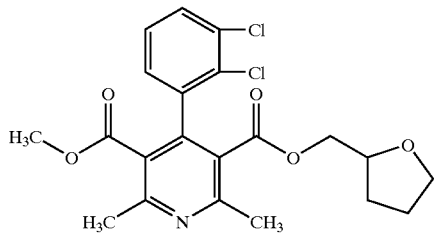

A) 4-(2,3-Dichlorophenyl)-2,6-dimethyl 1,4-dihydropyridine-3,5-dicarboxylic acid 3-methyl ester 5-(tetrahydrofuran-2-ylmethyl) ester A solution of 20 g (0.07 mol) of methyl 2,3-dichlorobenzylidenacetoacetate and 13.56 g (0.07 mol) de (tetrahydrofuran-2-ylmethyl) 3-aminocrotonate in 75 ml of abs. ethanol was refluxed with stirring for 8 hours, in the absence of light. The reaction mixture was then cooled to −10° C., and the resulting precipitate was filtered. The product, with a m.p. of 172–3° C. (EtOH), was obtained with a yield of 79%.

B) 4-(2,3-Dichlorophenyl)-2,6-dimethyl pyridine-3,5-dicarboxylic acid 3-methyl ester 5-(tetrahydrofuran-2-ylmethyl) ester To a suspension of 82 g (0.068 mol) of pyridinium chlorochromate on alumina in 230 ml of $CH_2Cl_2$, 10 g (0.023 mol) of 4-(2,3-dichlorophenyl)-2,6-dimethyl 1,4-dihydropyridine-3,5-dicarboxylic acid 3-methyl ester 5-(tetrahydrofuran-2-ylmethyl) ester were added, and the mixture was maintained with strong stirring during 7 hours. The insoluble solid was filtered and the remaining liquid was washed with water (3×250 ml), dried with anh. $Na_2SO_4$ and concentrated at low pressure. Finally, the product was obtained as an oil, with a yield of 87%.

Analysis Calculated for $C_{21}H_{21}Cl_2NO_5$

|  | % C | % H | % N |
|---|---|---|---|
| Calc. | 57.55 | 4.83 | 3.20 |
| Obs. | 57.32 | 5.05 | 3.08 |

Example 7

4-(2-Bromophenyl)-2,6-dimethyl pyridine-3,5-dicarboxylic acid 3-methyl ester 5-(tetrahydrofuran-2-ylmethyl) ester

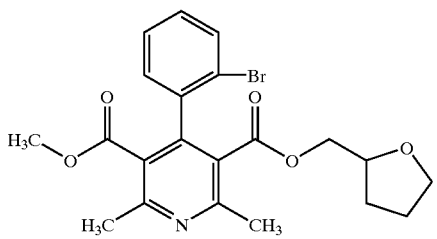

A) 4-(2-Bromophenyl)-2,6-dimethyl-1,4-dihydropyridine-3,5-dicarboxylic acid 3-methyl ester 5-(tetrahydrofuran-2-ylmethyl) ester A solution of 15 g (0.05 mol) of methyl 2-bromobenzylideneacetoacetate and 9.81 g (0.05 mol) of (tetrahydrofuran-2-ylmethyl)-3-aminocrotonate in 55 ml of ethanol, was refluxed in the absence of light for 10 hours. The mixture was then cooled to −10° C., and a yellow solid was obtained (mp 170–2° C., EtOH) with a yield of 85%.

B) 4-(2-Bromophenyl)-2,6-dimethyl pyridine-3,5-dicarboxylic acid 3-methyl ester 5-(tetrahydrofuran-2-ylmethyl) ester A mixture of 10 g (0.022 mol) of 4-(2-bromophenyl)-2,6-dimethyl-1,4-dihydropyridine-3,5-dicarboxylic acid 3-methyl ester 5-(tetrahydrofuran-2-ylmethyl) ester, obtained according A), and 80 g (0.067 mol) of pyridinium chlorochromate absorbed on alumina, was suspended on 220 ml of $CH_2Cl_2$, and the mixture was stirred at room temperature for 6 hours.

The remaining solid was eliminated by filtration, and the liquid was washed with water (3×150 ml), dried over anh. $Na_2SO_4$, and concentrated at reduced pressure, to dryness. The product was obtained as an oil, which was purified by column chromatography (Silicagel, n-hexane:EtAcO, 8:2) with a yield of 66%.

Analysis Calculated for $C_{21}H_{22}BrNO_5$

|       | % C   | % H  | % N  |
|-------|-------|------|------|
| Calc. | 56.26 | 4.95 | 3.12 |
| Obs.  | 56.21 | 5.17 | 3.08 |

Example 8

4-(3-Bromophenyl)-2,6-dimethyl pyridine-3,5-dicarboxylic acid 3-methyl 5-tetrahydrofuran-2-ylmethyl) ester

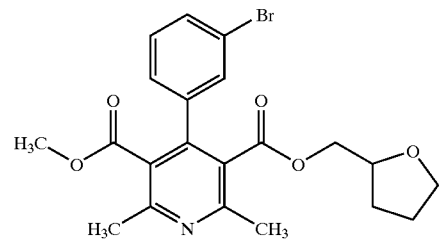

A) 4-(3-Bromophenyl)-2,6-dimethyl-1,4-dihydropyridine-3,5-dicarboxylic acid 3,5-di(tetrahydrofuran-2-ylmethyl) ester A solution of 15 g (0.05 mol) of methyl 3-bromobenzylideneacetoacetate and 9.81 g (0.05 mol) of (tetrahydrofuran-2-ylmethyl)-3-aminocrotonate in 55 ml of abs ethanol, was refluxed with stirring, in the absence of light, for 10 hours. The reaction mixture was then cooled to −10° C., yielding a white solid (mp 138–40° C., EtOH) with a yield of 85%.

B) 4-(3-Bromophenyl)-2,6-dimethylpyridine-3,5-dicarboxylic acid 3,5-(di(tetrahydrofuran-2-ylmethyl) ester A mixture of 10 g (0.022 mol) de 4-(3-bromophenyl)-2,6-dimethyl-1,4-dihydropyridine-3,5-dicarboxylic acid 3,5-di(tetrahydrofuran-2-ylmethyl) ester obtained as described in A), and 80 g (0.067 mol) of pyridinium chlorochromate adsorbed on alumina, was suspended in 220 ml of $CH_2Cl_2$, and the suspension was stirred at room temperature for 5 hours. The insoluble solid was eliminated by filtration, and the liquid was washed with water (3×200 ml), dried over anh. $Na_2SO_4$, and concentrated at reduced pressure, to dryness. The product was obtained as an oil, which was purified by column chromatography (Silicagel, n-hexane:EtAcO, 8:2) with a yield of 74%.

Analysis Calculated for $C_{21}H_{22}BrNO_5$

|       | % C   | % H  | % N  |
|-------|-------|------|------|
| Calc. | 56.26 | 4.95 | 3.12 |
| Obs.  | 56.62 | 4.88 | 3.38 |

Example 9

2,6-Dimethyl-4-(2-trifluoromethylphenyl) pyridine-3,5-dicarboxylic acid 3-methyl ester 5-(tetrahydrofuran-2-ylmethyl) ester A) 2,6-Dimethyl-4-(2-trifluoromethylphenyl)-1,4-dihydropyridine-3,5-dicarboxylic acid 3-methyl ester 5-(tetrahydrofuran-2-ylmethyl) ester

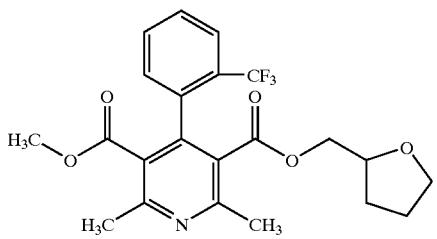

A solution of 90 ml (118.8 g; 0.68 mol) of 2-trifluoromethyibenzaldehyde, 75 ml (79.23 g; 0.68 mol) of methyl acetoacetate and 126.38 g (0.68 mol) of (tetrahydrofuran-2-ylmethyl)-3-aminocrotonate in 700 ml of 2-propanol, was refluxed in the absence of light along 10 hours.

Then, 400 ml of solvent were distilled off at reduced pressure, and the remaining solution was cooled at −10° C. In that way, a yellow solid was obtained (mp 147–9° C., MeOH) with a yield of 69%.

B) 2,6-Dimethyl-4-(2-trifluoromethylphenyl) pyridine-3,5-dicarboxylic acid 3-methyl ester 5-(tetrahydrofuran-2-ylmethyl) ester A mixture of 7 g (0.016 mol) of 2,6-dimethyl-4-(2-trifluoromethylphenyl)-1,4-dihydropyridine-3,5-dicarboxylic acid 3-methyl ester 5-(tetrahydrofuran-2-ylmethyl) ester, obtained according A),
and 57.35 g (0.048 mol) of pyridinium chlorochromate adsorbed on alumina, were suspended on 150 ml of $CH_2Cl_2$, then the whole mixture was maintained with stirring at room temperature for 8 hours. The remaining solid was eliminated by filtration, and the liquid was washed with water (3×150 ml), dried over $Na_2SO_4$, and concentrated at reduced pressure, to dryness. The product was obtained as an oil, which was purified by column chromatography (Silicagel, n-hexane:EtAcO, 8:2) with a yield of 69%.

Analysis Calculated for $C_{22}H_{22}F_3NO_5$

|  | % C | % H | % N |
| --- | --- | --- | --- |
| Calc. | 60.41 | 5.07 | 3.20 |
| Obs. | 60.11 | 5.31 | 3.29 |

Example 10

2,6-Dimethyl-4-(3-trifluoromethylphenyl) pyridine-3,5-dicarboxylic acid 3-methyl ester 5-(tetrahydrofuran-2-ylmethyl) ester

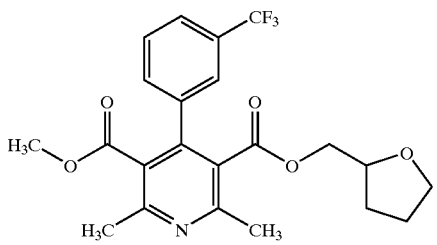

A) 2,6-Dimethyl-4-(3-trifluoromethylphenyl)-1,4-dihydropyridine-3,5-dicarboxylic acid 3-methyl ester 5-(tetrahydrofuran-2-ylmethyl) ester A solution of 13.21 g (0.05 mol) of methyl 3-trifluoromethylbenzylideneacetoacetate and 8.99 g (0.05 mol) of (tetrahydrofuran-2-ylmethyl)-3-aminocrotonate in 50 ml of abs ethanol, was refluxed under stirring, and protected from light, for 10 hours. The solvent was then evaporated under reduced pressure, and the residue was crystallised in EtAcO (15 ml). The product was obtained as a white solid (mp 108–10° C., EtOH), with a yield of 88%.

B) 2,6-Dimethyl-4-(3-trifluoromethylphenyl) pyridine-3,5-dicarboxylic acid 3-methyl ester 5-(tetrahydrofuran-2-ylmethyl) ester A mixture of 12 g (0.027 mol) of 2,6-dimethyl-4-(3-trifluoromethylphenyl)-1,4-dihydropyridine-3,5-dicarboxylic acid 3-methyl ester 5-(tetrahydrofuran-2-ylmethyl) ester, obtained as described in A), and 98 g (0.082 mol) of pyridinium chlorochromate adsorbed on alumina, was suspended in 270 ml of $CH_2Cl_2$, and the suspension was maintained under stirring at room temperature for 6 hours. The remaining solid was eliminated by filtration, and the liquid was washed with water (3×300 ml), drive over anh. $Na_2SO_4$, and concentrated at reduced pressure, to dryness. The product was obtained as an oil, which was purified by column chromatography (Silicagel, n-hexane:EtAcO, 8:2) with a yield of 65%.

Analysis Calculated for $C_{22}H_{22}F_3NO_5$

|  | % C | % H | % N |
| --- | --- | --- | --- |
| Calc. | 60.41 | 5.07 | 3.20 |
| Obs. | 60.02 | 5.01 | 3.51 |

Example 11

4-(3-Cyanophenyl)-2,6-dimethyl pyridine-3,5-dicarboxylic acid 3-methyl ester 5-(tetrahydrofuran-2-ylmethyl) ester

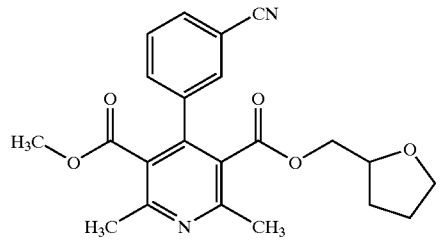

A) 4-(3-Cyanophenyl)-2,6-dimethyl 1,4-dihydropyridine-3,5-dicarboxylic acid 3-methyl ester 5-(tetrahydrofuran-2-ylmethyl) ester A solution of 30 g (0.13 mol) of methyl 3-cyanobenzylideneacetoacetate and 24.24 g (0.13 mol) of (tetrahydrofuran-2-ylmethyl)-3-aminocrotonate in 130 ml of abs. ethanol was refluxed with stirring, in the absence of light, along 8 hours. The reaction mixture was then cooled to −10° C., and the product was obtained as a yellow solid (mp 127–9° C., EtOH) with a yield of 79%.

B) 4-(3-Cyanophenyl)-2,6-dimethyl pyridine-3,5-dicarboxylic acid 3-methyl ester 5-(tetrahydrofuran-2-ylmethyl) ester A mixture of 10 g (0.025 mol) of 4-(3-cyanophenyl)-2,6-dimethyl 1,4-dihydropyridine-3,5-dicarboxylic acid 3-methyl ester 5-(tetrahydrofuran-2-ylmethyl) ester, obtained as described in A), and 91 g (0.076 mol) of pyridinium chlorochromate adsorbed on alumina, was suspended on 250 ml of CH₂Cl₂, and the suspension was stirred at room temperature for 5 hours. The remaining solid was separated by filtration, and the organic solution was washed with water (3×150 ml), dried with anh. Na₂SO₄, and concentrated to dryness at reduced pressure. The product was obtained as an oil, which was purified by column chromatography (Silicagel, n-hexane:EtAcO, 8:2) with a yield of 78%.

Analysis Calculated for $C_{22}H_{22}N_2O_5$

|  | % C | % H | % N |
| --- | --- | --- | --- |
| Calc. | 66.99 | 5.62 | 7.10 |
| Obs. | 66.84 | 5.92 | 7.14 |

Example 12

2,6-Dimethyl-4-(2-nitrophenyl) pyridine-3,5-dicarboxylic acid 3-methyl ester 5-(tetrahydrofuran-2-ylmethyl) ester

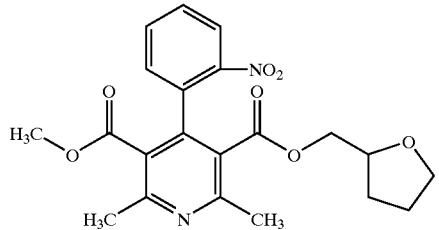

To a solution of 30 g (0.07 mol) of 2,6-dimethyl-4-(2-nitrophenyl)-1,4-dihydropyridine-3,5-dicarboxylic acid 3-methyl ester 5-(tetrahydrofuran-2-ylmethyl) ester in 72 ml of acetic acid, heated to reflux, 7.2 g (0.07 mol) of CrO₃ were portionwise added. After the addition was complete, reflux was maintained for one additional hour. The reaction mixture was then slowly poured on ice-cooled aq NH₄OH (150 ml). The mixture separated in two phases, and it was evacuated with CH₂Cl₂ (3×100 ml). The organic extract was dried with anh Na₂SO₄, and concentrated to dryness at reduced pressure. The resulting oil was crystallised in EtAcO-diethylether, yielding a white solid (mp 69–70° C., EtOH) with a yield of 79%.

Analysis Calculated for $C_{21}H_{22}N_2O_7$

|  | % C | % H | % N |
| --- | --- | --- | --- |
| Calc. | 60.86 | 5.35 | 6.76 |
| Obs. | 60.63 | 5.26 | 6.52 |

Example 13

(S)-2,6-(Dimethyl-4-(2-nitrophenyl) pyridine-3,5-dicarboxylic acid 3-methyl ester 5-(tetrahydrofuran-2-ylmethyl) ester

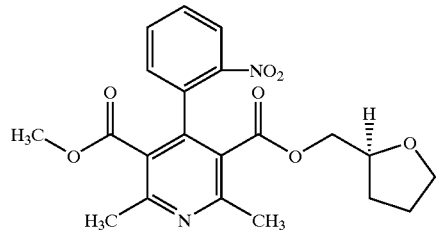

Over a stirred solution of 1.183 g (2.84 mmol) of (R/S)-2,6-Dimethyl-4-(2-nitrophenyl)-1,4-dihydropyridine-3,5-dicarboxylic acid 3-methyl ester 5-(S-tetrahydrofuran-2-ylmethyl) ester in 4 ml of acetic acid, 588 mg (8.53 mmol) of sodium nitrite was portionwise added, at room temperature. Once the addition completed, the reaction mixture was maintained with stirring at 50° C., during 90 min. Then, the reaction mixture was poured over 20 ml of ice/water, and then it was neutralised (to pH 5) with 20% aq NAOH, and then (to pH 7) with NaHCO₃. The solution was then extracted with CH₂Cl₂ (2×25 ml), and the organic extract was washed with a saturated solution of NaCl, dried over anh. Na₂SO₄, and concentrated at reduced pressure, to dryness. The product was obtained as an oil, which was purified by column chromatography (Silicagel, n-hexane:EtAcO, 1:1). In that way, 879 mg of the product were obtained (yield:74%). The hydrobromide was prepared by treating an ethanolic solution of the product with 48% HBr, obtaining a white solid (121–4° C., EtOH).

Mass Spectra
M/e: 384(4); 368(20); 331(19); 315(25); 284(25); 270(15); 267(27); 253(34); 236(42); 235(25); 209(25); 180 (20); 153(28); 152(38); 140(33); 139(38); 128(35); 127(43); 126 (30); 114(33); 102(23); 101(25); 85 (156); 84(543); 77(33); 76(26); 71(1000); 67(35); 55(38).

Example 14

(R)-2,6-Dimethyl-4-(2-nitrophenyl) pyridine-3,5-dicarboxylic acid 3-methyl ester 5-(tetrahydrofuran-2-ylmethyl)ester

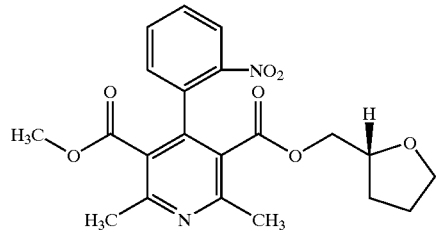

Over a solution of 0.89 g (2.13 mmol) of (R/S)-2,6-dimethyl-4-(2-nitrophenyl)-1,4-dihydropyridine-3,5-dicarboxylic acid 3-methyl ester 5-(R-tetrahydrofuran-2-ylmethyl) ester on 4 ml of acetic acid, stirred and heated to 60° C., 442 mg (6.41 mmol) of sodium nitrite was portionwise added. Once the addition was finished, stirring and heating were maintained for 90 min. more. Then, the reaction mixture was poured over 20 ml of ice/water, and then it was neutralised (to pH 5) with 20% aq NAOH, and then (to pH 7) with NaHCO₃. The solution was then extracted with CH₂Cl₂ (2×25 ml), and the organic extract was washed with a saturated solution of NaCl, dried over anh. N2₂SO₄, and concentrated at reduced pressure, to dryness. The product was obtained as an oil, which was purified by column chromatography (Silicagel, n-hexane:EtAcO, 6:4). In that way, 334 mg of the product were obtained (yield: 38%). The hydrobromide was prepared by treating an ethanolic solution of the product with 48% HBr, obtaining a white solid (114–6° C., EtOH).

Mass Spectra

M/e:,383(3); 368(16); 331(13); 315(20); 284(21); 270(14); 253(27); 236(34); 235(20); 209(20); 180(19); 153(25); 152 (33); 140(30); 139(33); 128(33); 127(37); 126(27); 102(22); 101(23); 85(149); 84(514); 77(29); 76(27); 71(1000); 55(46).

Example 15

2,6-Dimethyl-4-(2-nitrophenyl) pyridine-3,5-dicarboxylic acid 3-methyl ester 5-(5-oxotetrahydrofuran-2-ylmethyl)ester

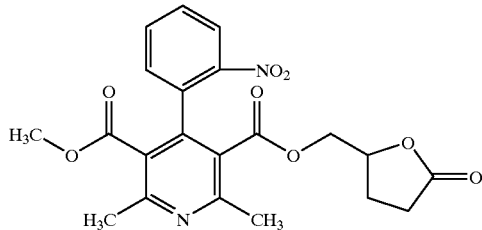

A) 2,6-Dimethyl-4-(2-nitrophenyl)-1,4-dihydropyridine-3,5-dicarboxylic acid 3-methyl ester 5-(5-oxotetrahydrofuran-2-ylmethyl) ester A solution of 10 g (0,03 mol) of (5-oxotetrahydrofuran-2-ylmethyl) 2-nitrobenzylideneacetoacetate and 3.5 g (0,03 mol) of methyl 3-aminocrotonate in 30 ml of abs. ethanol, was refluxed with stirring in the absence of light, along 10 hours. The solvent was then distilled off at reduced pressure, and the obtained residue was purified by column chromatography (Silicagel, toluene:EtAcO, 1:1). In that way, the product was isolated as an oil, which crystallised in diisopropylether (5 ml), yielding a yellow solid (mp 86–8° C., diisopropyl ether) with a yield of 68%

B) 2,6-Dimethyl-4-(2-nitrophenyl) pyridine-3,5-dicarboxylic acid 3-methyl ester 5-(5-oxotetrahydrofuran-2-ylmethyl) ester Over a boiling solution of 15 g (0,035 mol) of 2,6-dimethyl-4-(2-nitrophenyl)-1,4-dihydropyridine-3,5dicarboxylic acid 3-methyl ester 5-(5-oxotetrahydrofuran-2-ylmethyl) ester, obtained according A), in 35 ml of acetic acid, 3,5 g (0,035 mol) of CrO₃ was portionwise added with stirring. Once the addition completed, reflux and stirring were maintained for one additional hour. Then, the reaction mixture was poured over 375 ml of conc. NH₄OH with ice, and the mixture was left overnight at 5° C. In that way, a solid was obtained (mp 132–4° C., MeOH) with a yield of 69%.

Analysis calculated for $C_{21}H_{20}N_2O_8$

|       | % C   | % H  | % N  |
|-------|-------|------|------|
| Calc. | 58.88 | 4.71 | 6.54 |
| Obs.  | 59.04 | 4.84 | 6.59 |

Example 16

2,6-Dimethyl-4-(3-nitrophenyl) pyridine-3,5-dicarboxylic acid 3-methyl ester 5-(tetrahydrofuran-2-ylmethyl) ester

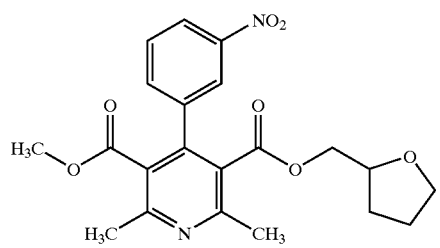

A mixture of 15 g (0.036 mol) of 2,6-dimethyl-4-(3-nitrophenyl)-1,4-diydropyridine-3,5-dicarboxylic acid 3-methyl ester 5-(tetrahydrofuran-2-ylmethyl) ester and 130 g (0.108 mol) of pyridinium chlorochromate adsorbed on alumina, was suspended on 360 ml of CH₂Cl₂, and maintained with stirring at room temperature for 8 hours. The remaining solid was eliminated by filtration and the organic solution was washed with water (3×300 ml), dried over anh. Na₂SO₄, and concentrated to dryness at reduced pressure. The product was obtained as an oil which was purified by column chromatography (Silicagel, n-hexane:EtAcO, 8:2) with a yield of 72%

Analysis calculated for $CH_{21}H_{22}N_2O_7$

|       | % C   | % H  | % N  |
|-------|-------|------|------|
| Calc. | 60.86 | 5.35 | 6.76 |
| Obs.  | 60.58 | 5.45 | 7.01 |

Example 17

2,6-Dimethyl-4-(3-nitrophenyl)-pyridine-3,5-dicarboxylic acid 3,5-di(tetrahydrofuran-2-ylmethyl) ester (hydrochloride)

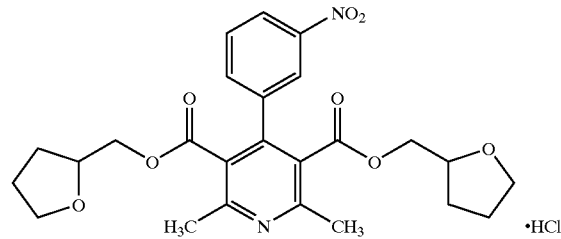

A) 2,6-Dimethyl-4-(3-nitrophenyl)-1,4-dihydropyridine-3,5-dicarboxylic acid 3,5-di(tetrahydrofuran-2-ylmethyl) ester A solution of 15 g (0.05 mol) of tetrahydrofuran-2-ylmethyl 3-nitrobenzylidenacetoacetate and 8.7 g (0.05 mol) of (tetrahydrofuran-2-ylmethyl)-3-aminocrotonate in 50 ml of abs ethanol, was refluxed with stirring, in the absence of light, along 8 hours. The reaction mixture was then cooled to −10° C. A yellow soild (mp 122–3° C., EtAcO) was obtained with a yield of 80%.

B) 2,6-Dimethyl-4-(3-nitrophenyl)-pyridine-3,5-dicarboxylic acid 3,5-di(tetrahydrofuran-2-ylmethyl) ester (hydrochloride)

A mixture of 8 g (0.016 mol) of 2,6-Dimethyl-4-(3-nitrophenyl)-1,4-dihydropyridine-3,5-dicarboxylic acid 3,5-di(tetrahydrofuran-2-ylmethyl) ester, obtained as described in A), and 60 g (0.049 mol) of pyridinium chlorochromate adsorbed on alumina, was suspended in 160 ml of $CH_2Cl_2$, and the mixture was maintained at room temp. with stirring for 6 hours. The solid was separated by filtration and the liquid was washed with water (3×200 ml), dried (anh $Na_2SO_4$), and concentrated at reduced pressure. The residue, obtained as an oil, was converted into hydrochloride by dissolving it into ethanol (10 ml) and then, adding HCl saturated ethyl ether (20 ml). The produce precipitated as a white solid (mp 75–77° C., EtOH-ether) with a yield of 67%.

Analysis calculated for $C_{25}H_{28}N_2O_8HCl$

|       | % C   | % H  | % N  |
|-------|-------|------|------|
| Calc. | 57.64 | 5.61 | 5.38 |
| Obs.  | 57.75 | 5.65 | 5.27 |

Example 18

4-(4-Chloro-3-nitrophenyl)-2,6-dimethyl pyridine-3,5-dicarboxylic acid 3-methyl ester 5-(tetrahydrofuran-2-ylmethyl) ester A) 4-(4-Chloro-3-nitrophenyl)-2,6-dimethyl-1,4-dihydropyridine-3,5-dicarboxylic acid 3-methyl ester 5-(tetrahydrofuran-2-ylmethyl) ester

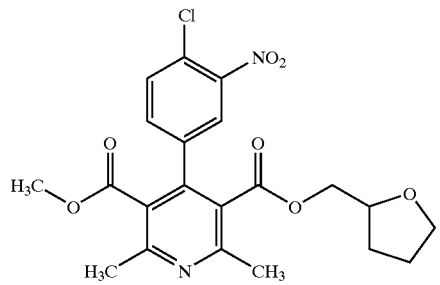

A solution of 20 g (0.07 mol) of methyl 4-chloro-3-nitrobenzylidenacetoacetate and 13.06 g (0.07 mol) of (tetrahydrofuran-2-ylmethyl)-3-aminocrotonate in 70 ml of abs ethanol, was refluxed with stirring, in the absence of light, for 8 hours. The solution was then concentrated to dryness at reduced pressure, and the residue was crystallised in EtAcO. A yellow solid was obtained (mp 148–50° C. EtOH) with a yield of 85%.

B) 4-(4-Chloro-3-nitrophenyl)-2,6-dimethyl pyridine-3,5-dicarboxylic acid 3-methyl ester 5-(tetrahydrofuran-2-ylmethyl)ester A mixture of 9 g (0.020 mol) of 4-(4-chloro-3-nitrophenyl)-2,6-dimethyl-1,4-dihydropyridine-3,5-dicarboxylic acid 3-methyl ester 5-(tetrahydrofuran-2-ylmethyl) ester, obtained as described in A) in 72 g (0.060 mol) of pyridinium chlorochromate adsorbed on alumina, were suspended on 200 ml of $CH_2Cl_2$ then, the mixture was maintained with stirring at room temperature for 9 hours. The remaining solid was filtered, and the filtrate was washed with water (3×200 ml), dried with anh. $Na_2SO_4$, and the solvent evaporated under reduced pressure. The product was isolated as an oil, which was purified by column chromatography (Silicagel, n-hexane:EtAcO, 8:2) with a yield of 69%.

Analysis calculated for $C_{21}H_{21}ClN_2O_7$

|       | % C   | % H  | % N  |
|-------|-------|------|------|
| Calc. | 56.19 | 4.72 | 6.24 |
| Obs.  | 56.17 | 4.78 | 6.59 |

Example 19

4-(3Acetylaminophenyl)-2,6-dimethyl pyridine-3,5-dicarboxylic acid 3-methyl ester 5-(tetrahydrofuran-2-ylmethyl) ester (hydrochloride)

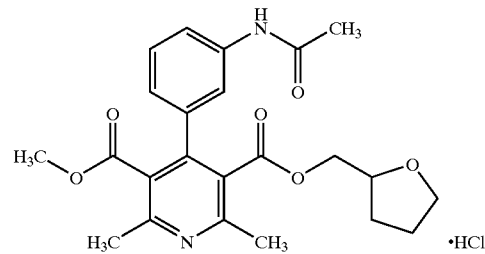

A) 4-(3-Acetylaminophenyl)-2,6-dimethyl-1,4-dihydropyridine-3,5-dicarboxylic acid 3-methyl ester 5-(tetrahydrofuran-2-ylmethyl) ester A solution of 30 g (0.115 mol) of methyl 3-acetylaminobenzylideneacetoacetate and 21.27 g (0.115 mol) of (tetrahydrofuran-2-ylmethyl)-3-aminocrotonate in 120 ml of isopropanol was heated to reflux with stirring along 8 hours, protected form the light. The solvent was evaporated under vacuum, and the residue was crystallised in ethyl acetate. A yellow solid was obtained, (MP 158–60° C., meow) with a yield of 76%.

B) 4-(3-Acetylaminophenyl)-2,6-dimethyl pyridine-3,5dicarboxylic acid 3-methyl ester 5-(tetrahydrofuran-2-ylmethyl) ester (hydrochloride)

A mixture of 12 g (0.03 mol) de 4-(3-Acetylaminophenyl)-2,6-dimethyl-1,4-dihydropyridine-3,5-dicarboxylic acid 3-methyl ester 5-(tetrahydrofuran-2-ylmethyl) ester, as indicated in A), and 4.87 g (0.056 mol) of $MnO_2$ suspended in 60 ml of methylisobutylketone was refluxed with stirring for 24 hours. The remaining solid was immediately filtered and the solution concentrated at low pressure. The residue obtained was dissolved in 250 ml of 5% aq HCl, the solution was extracted with EtAcO (3×10 ml) and then, pH of the aqueous layer was adjusted to 8 with 20% $K_2CO_3$. The aqueous phase then, was extracted with $CH_2Cl_2$ (3×100 ml), the organic extracts were dried over anh. $Na_2SO_4$, concentrated at reduced pressure, and a yellow oil was obtained, which was transformed in hydrochloride by dissolving it in ethanol (10 ml) and adding HCl saturated diethyl ether (20 ml). In that way, a white solid was obtained (mp 196–8° C., MeOH) with a yield of 59%.

Analysis calculated for $C_{23}H_{26}N_2O_6HCl$

|  | % C | % H | % N |
|---|---|---|---|
| Calc. | 59.67 | 5.88 | 6.05 |
| Obs. | 59.56 | 6.12 | 5.92 |

Example 20

2,6-Dimethyl-4-(3-hydroxyphenyl) pyridine-3,5-dicarboxylic acid 3-methyl ester 5-(tetrahydrofuran-2-ylmethyl) ester (hydrochloride)

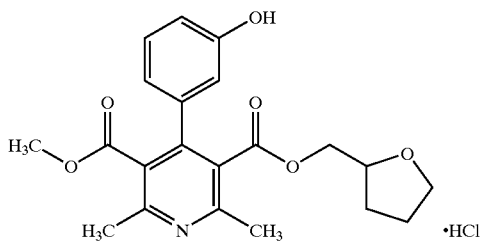

A) 2,6-Dimethyl-4-(3-hydroxyphenyl) 1,4-dihydropyridine-3,5-dicarboxylic acid 3-methyl ester 5-(tetrahydrofuran-2-ylmethyl) ester A solution of 15 g (0.07 mol) of methyl 3-hydroxybenzylideneacetoacetate and 12.62 g (0.07 mol) of (tetrahydrofuran-2-ylmethyl)-3-aminocrotonate in 70 ml of abs. ethanol, was refluxed with stirring for 8 hours in the absence of light. The solvent was evaporated at reduced pressure, and the residue was crystallised in EtAcO. In that way, a yellow solid was obtained (mp 170–2° C., EtAcO) with a yield of 82%.

B) 2,6-Dimethyl-4-(3-hydroxyphenyl) pyridine-3,5-dicarboxylic acid 3-methyl ester 5-(tetrahydrofuran-2-ylmethyl) ester (hydrochloride)

A mixture of 10 g (0.026 mol) of 2,6-Dimethyl-4-(3-hydroxyphenyl) 1,4-dihydropyridine-3,5-dicarboxylic acid 3-methyl ester 5-(tetrahydrofuran-2-ylmethyl) ester, obtained as indicated in A), and 2.6 g (0.030 mol) of $MnO_2$ in 50 ml of methylisobutylketone, was refluxed with stirring for 14 hours. The remaining solid was eliminated by filtration, and the liquid was concentrated to dryness under reduced pressure. The residue obtained was dissolved in 15 ml of 15% aq. HCl, then, the solution was washed with ethyl acetate (10 ml), the pH was adjusted to 8 with 20% aq. $K_2CO_3$. Finally, the solution was extracted with $CH_2Cl_2$ (2×50 ml), the organic extracts were dried over anh $Na_2SO_4$, and concentrated to dryness at reduced pressure. The residue appeared as an oil, which crystallised in 2 ml of methanol, and was transformed into the hydrochloride by dissolution in ethanol (10 ml) and addition of HCl saturated diethyl ether (20 ml). A yellow solid was obtained (mp 95–7° C., MeOH) with a yield of 64%.

Analysis calculated for $C_{21}H_{23}NO_6HCl$

|  | % C | % H | % N |
|---|---|---|---|
| Calc. | 59.79 | 5.73 | 3.32 |
| Obs. | 59.64 | 5.66 | 3.23 |

Example 21

2,6-Dimethyl-4-(2,3-dimethoxyphenyl) pyridine-3,5-dicarboxylic acid 3-methyl ester 5-(tetrahydrofuran-2-ylmethyl) ester

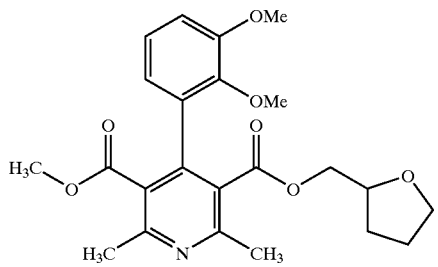

A mixture of 11 g (0,025 mol) of 2,6-dimethyl-4-(2,3-dimethoxyphenyl)-1,4-dihydropyridine-3,5-dicarboxylic acid 3-methyl ester 5-(tetrahydrofuran-2-ylmethyl) ester and 92 g (0,076 mol) of pyridinium chlorochromate absorbed on alumina, was suspended on 250 ml of $CH_2Cl_2$, and the whole mixture was maintained on stirring at room temperature for 6 hours. The remaining solid was eliminated by filtration, and the liquid was washed with water (3×300 ml), dried over anh. $Na_2SO_4$, and concentrated at reduced pressure, to dryness. The product was obtained as an oil, which was purified by column chromatography (Silicagel, n-hexane:EtAcO, 8:2) with a yield of 79%.

Analysis calculated for $C_{23}H_{27}NO_7$

|  | % C | % H | % N |
|---|---|---|---|
| Calc. | 64.32 | 6.34 | 3.26 |
| Obs. | 64.34 | 6.36 | 3.28 |

The compounds described in the examples 22 to 30 have been obtained as previously described in the literature.

Example 22

2,6-Dimethyl-4-(3-nitrophenyl)-pyridine-3,5-dicarboxylic acid 3-isopropyl ester 5-(2-methoxyethyl) ester

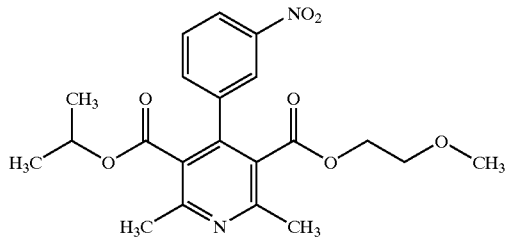

Example 23

2,6-Dimethyl-4-(2-nitrophenyl)-pyridine-3,5-dicarboxylic acid 3-methyl ester 5-isobutyl ester

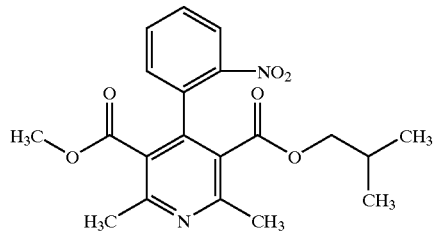

Example 24

2,6-Dimethyl-4-(3-nitrophenyl)pyridine-3,5-dicarboxylic acid 3-ethyl 5-methyl ester

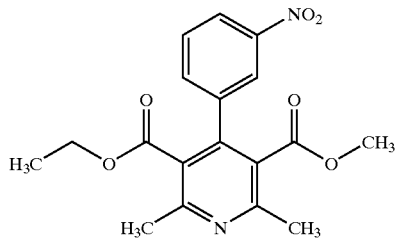

Example 25

2,6-Dimethyl-4-(2-nitrophenyl) pyridine-3,5-dicarboxylic acid dimethyl ester

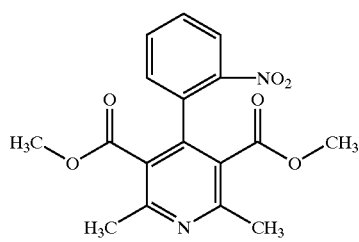

Example 26

4-[2-(2-tert-Butoxycarbonylvinyl)-phenyl]-2,6-dimethyl pyridine-3,5-dicarboxylic acid diethyl ester

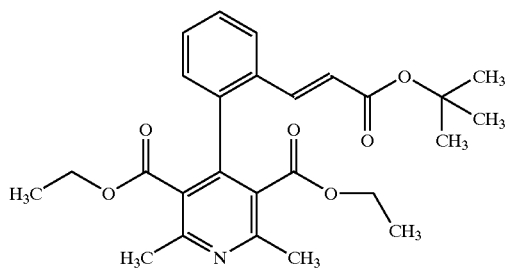

Example 27

2,6-Dimethyl-4-(3-nitrophenyl) pyridine-3,5-dicarboxylic acid 3-methyl ester 5-(N-methylbenzylamino)ethyl ester

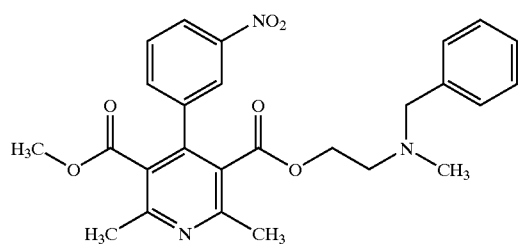

Example 28

4-(2,3-Dichlorophenyl)-2,6-dimethyl pyridine-3,5dicarboxylic acid 3-ethyl ester 5-methyl ester

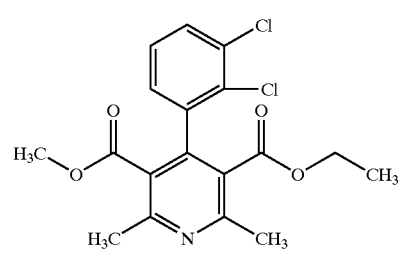

Example 29

2-(2-Aminoethoxy)methyl-4-(2-chlorophenyl)-6-methylpyridine-3,5-dicarboxylic acid 3-ethyl ester 5-methyl ester

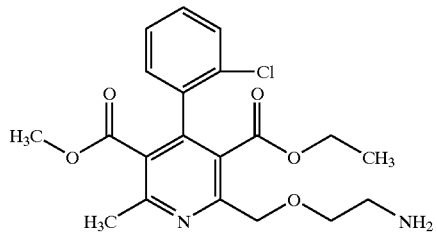

Example 30

2,6-Dimethyl-4-(3-nitrophenyl) pyridine-3,5-dicarboxylic acid 3-(2-methoxyethyl) ester 5-(3-phenyl)propen-2-yl ester

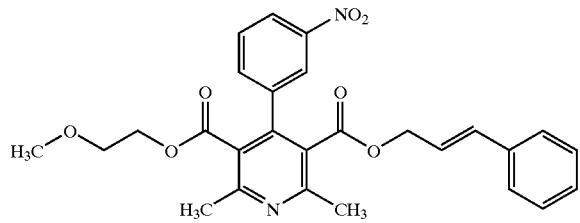

Example 31

2,6-Dimethyl-4-(2-nitrophenyl) pyridine-3,5-dicarboxylic acid 3-methyl ester

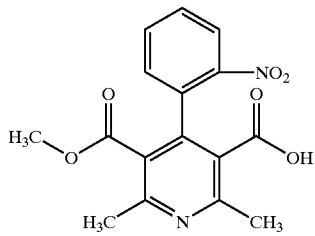

A) 2,6-Dimethyl-4-(2-nitrophenyl) pyridine-3,5-dicarboxylic acid 3,5-dimethyl ester Over a boiling solution of 3 kg (8.7 mol) of 2,6-dimethyl-4-(2nitrophenyl)-1,4-dihydropyridine-3,5-dicarboxylic acid 3,5-dimethyl ester in 8,25 l of acetic acid, 870 g (8.7 mol) of $CrO_3$ were portionwise added, with stirring. When the addition was complete, the reaction mixture was refluxed with stirring for one additional hour. When the mixture reached the room temperature, it was slowly poured, with stirring, over 22.5 l of a mixture of 25% aq. $H_4NOH$ and ice (2:1), and the product precipitated. The solid was isolated by filtration, washed with water until neutral pH, and crystallised (mp 99–101° C., MeOH) with a yield of 83%.

B) 2,6-Dimethyl-4-(2-nitrophenyl) pyridine-3,5-dicarboxylic acid 3-methyl ester

A solution of 500 g of 2,6-dimethyl-4-(2-nitrophenyl) pyridine-3,5-dicarboxylic acid 3,5-dimethyl ester (1.5 mol) and 87.5 g of KOH (1.32 mol) in 5 l of methanol and 1.5 l of water, was refluxed with stirring for 4 hours. Then, the solvent was eliminated at reduced pressure and the remaining residue was triturated with 1 l of water. The solid (mostly unreacted starting material) was eliminated by filtration, and the filtrate was treated, at 0° C., slowly and with stirring, with 100 ml of 35% aq. HCl, and the mixture was maintained with stirring for one additional hour with stirring, at room temperature. A solid was formed, which was washed with water (250 ml) and ethanol (250 ml), yielding a yellowish solid (mp 232–3° C., ethanol) with a yield of 70%. A small percentage (12%) of the diacid corresponding to example 32, was isolated from the mother liquids.

Analysis calculated for $C_{16}H_{14}N_2O_6$

|       | % C   | % H  | % N  |
|-------|-------|------|------|
| Calc. | 58.18 | 4.27 | 8.48 |
| Obs.  | 58.30 | 4.49 | 8.62 |

Example 32

2,6-Dimethyl-4-(2-nitrophenyl) pyridine-3,5-dicarboxylic acid

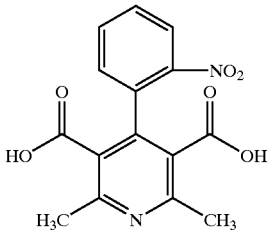

Example 33

2,6-Dimethyl-4-(2-nitrophenyl) pyridine-3,5-dicarboxylic acid 3-(2-dimethylaminoethyl) ester 5-methyl ester (dihydrobromide)

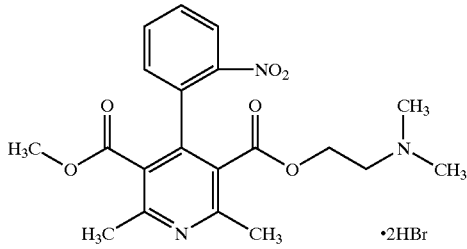

A) Snythesis of 5-chlorocarbonyl-2,6-dimethyl-4-(2nitrophenyl)pyridine-3-carboxylic acid methyl ester Over a mixture of 2,5 g (7,5 mmol) of 2,6-dimethyl-4-(2-nitrophenyl) pyridine-3,5-dicarboxylic acid 3-methyl ester and 0,7 g (3,8 mmol) of cianuryl chloride, in 20 ml of anh. acetone under argon atmosphere, 1.1 ml of triethylamine were added. The resulting mixture was maintained with stirring at room temperature along 7 hours. Then, the mixture was concentrated to dryness at reduced pressure, and the residue was purified by column chromatography (Silicagel, n-hexane:EtAcO, 1:1) with a yield of 80%.

B) 2,6-Dimethyl-4-(2-nitrophenyl) pyridine-3,5-dicarboxylic acid 3-(2dimethylaminoethyl) ester 5-methyl ester (dihydrobromide) Over a mixture of 0,169 (1,8 mmol) of N-dimethylaminoethanol and 0,20 ml of triethylamine in 8 ml of $CH_2Cl_2$, cooled to 0° C. and in argon atmosphere, 0,5 g (1,5 mmol) of 5-chlorocarbonyl-2,6-dimethyl-4-(2-nitro-phenyl)pyridine-3-carboxylic acid methyl ester described in A), dissolved in 4 of $CH_2Cl_2$ were added. The reaction mixture was stirred overnight at room temperature. Then, the mixture was washed with water, dried over anh. $Na_2SO_4$, and concentrated to dryness at reduced pressure. The product was obtained as an oil, which was converted in dihydrobromide by treatment with EtOH (10 ml) and conc. HBr (1 ml). A white solid was obtained (85–8° C., EtOH) with a yield of 73%.

Analysis calculated for $C_{20}H_{23}N_3O_6HBr$

|  | % C | % H | % N |
|---|---|---|---|
| Calc. | 49.89 | 5.03 | 8.73 |
| Obs. | 49.62 | 5.47 | 9.02 |

Example 34

2,6-Dimethyl-4-(2-nitrophenyl) pyridine-3,5-dicarboxylic acid 3-(2-diethylaminoethyl) ester 5-methyl ester (dihydrochloride)

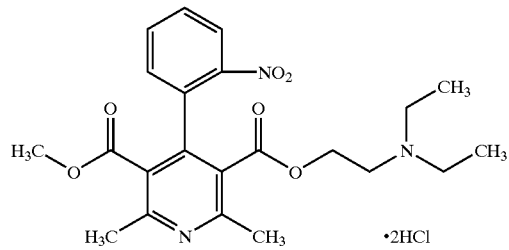

Over a solution of 0,37 g (3,1 mmol) of N-diethylaminoethanol and 0,20 g (2,86 mmol) of triethylamine in 10 ml of $CH_2Cl_2$, cooled to 0° C., and under nitrogen atmosphere, 1 g (2,86 mmol) of 5-chlorocarbonyl-2,6-dimethyl-4-(2-nitro-phenyl)pyridine-3-carboxylic acid methyl ester, obtained as described in A) of the example 33, dissolved in 8 ml of $CH_2Cl_2$, were added. The mixture was stirred at room temperature for 15 hours; then, it was washed with water (10 ml), dried over anh. $Na_2SO_4$, and concentrated at reduced pressure, to dryness. The product was obtained as an oil, which was purified by column chromatography (Silicagel, EtAcO) and converted into dihydrochloride by treatment with EtOH (10 ml) and conc. HCl (1 ml). A white solid was obtained (166–7° C., EtOH) with a yield of 71%.

Analysis calculated for $C_{22}H_{27}N_3O_6 2HCl$

|  | % C | % H | % N |
|---|---|---|---|
| Calc. | 52.68 | 5.83 | 8.38 |
| Obs. | 52.96 | 5.56 | 8.07 |

Example 35

2,6-Dimethyl-4-(2-nitrophenyl) pyridine-3,5-dicarboxylic acid 5-(3-dimethylaminopropyl) 3-methyl ester (dihydrochloride)

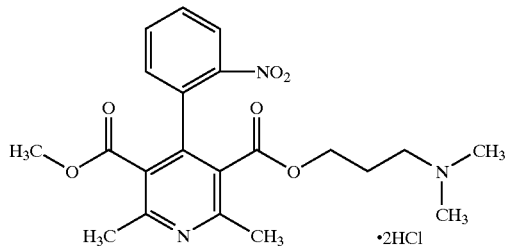

Over a solution of 0,146 g (1,4 mmol) of 3-dimethylamino-1-propanol and 0,13 g (1,29 mmol) of triethylamine in 6 ml of $CH_2Cl_2$, cooled to 0° C. and under nitrogen atmosphere, 0,45 g (1,29 mmol) of 5-chlorocarbonyl-2,6-dimethyl-4-(2-nitro-phenyl)pyridine-3-carboxylic acid methyl ester, obtained as described in A) of the example 33, dissolved in 5 ml of $CH_2Cl_2$, were added. The mixture was stirred at room temperature along 15 hours; then, it was washed with water (10 ml), dried over anh. $Na_2SO_4$, and concentrated at reduced pressure, to dryness. The product was obtained as an oil, which was purified by column chromatography (Silicagel, acetone) and converted into dihydrochloride by treatment with EtOH (10 ml) and conc. HCl (1 ml). A white solid was obtained (164–6° C., EtOH) with a yield of 75%.

Analysis calculated for $C_{21}H_{25}N_3O_6 2HCl$

|  | % C | % H | % N |
|---|---|---|---|
| Calc. | 51.73 | 5.59 | 8.62 |
| Obs. | 51.50 | 5.82 | 8.43 |

Example 36

2,6-Dimethyl-4-(2-nitrophenyl) pyridine-3,5-dicarboxylic acid 3-methyl ester 5-(N-morpholino) ethyl ester (dihydrochloride)

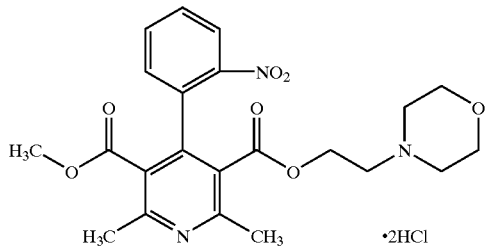

Over a solution of 0,21 g (1,57 mmol) of N-(2-hydroxyethyl)-4-morpholine and 0,15 g of triethylamine in 5 ml of $CH_2Cl_2$, cooled to 0° C. and under argon atmosphere, 0,5 g (1,43 mmol) of 5-chlorocarbonyl-2,6-dimethyl-4-(2-nitro-phenyl)pyridine-3-carboxylic acid methyl ester, obtained as described in A) of the example 33, dissolved in 4 ml of $CH_2Cl_2$, were added. The reaction mixture was stirred at room temperature along 12 hours,;

then, it was washed with water (10 ml), dried over anh. $Na_2SO_4$, and concentrated at reduced pressure, to dryness. The product was obtained as an oil, which was purified by column chromatography (Silicagel, EtAcO) and converted into dihydrochloride by treatment with EtOH (10 ml) and conc. HCl (1 ml). A white solid was obtained (mp 96–8° C., EtOH) with a yield of 51%.

Analysis calculated for $C_{22}H_{25}N_3O_7 \cdot 2HCl$

|       | % C   | % H  | % N  |
|-------|-------|------|------|
| Calc. | 51.25 | 5.28 | 8.16 |
| Obs.  | 51.48 | 5.11 | 8.00 |

Example 37

2,6-Dimethyl-4-(2-nitrophenyl)pyridine-3,5-dicarboxylic acid 3-methyl ester 5-[1,3-di(N-morpholine)isopropyl] ester trihydrochloride

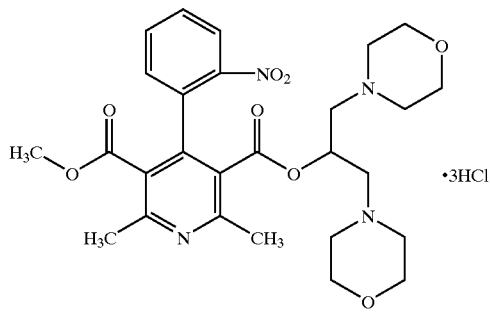

A mixture of 0.34 g (0.86 mmol) of 5-chlorocarbonyl-2,6-dimethyl-4-(2-nitro-phenyl)pyridine-3-carboxylic acid methyl ester, obtained as described in A) of the example 33, 0.22 g (0.95 mmol) of 1,3-dimorpholin-4-yl-propan-2-ol and 96 mg (0.86 mmol) of triethylamine, were stirred at room temperature for 12 hours. Then, the mixture was washed with water (10 ml), dried over anh. $Na_2SO_4$, and concentrated at reduced pressure to dryness. The product was obtained as an oil, which was purified by column chromatography (Silicagel, EtAcO) and converted into trihydrochloride by treatment with EtOH (10 ml) and conc. HCl (1 ml). A white solid was obtained (mp 187–92° C., EtOH) with a yield of 24%.

Analysis calculated for $C_{27}H_{34}N_4O_8 \cdot 3HCl$

|       | % C   | % H  | % N  |
|-------|-------|------|------|
| Calc. | 49.83 | 5.74 | 8.61 |
| Obs.  | 49.48 | 5.61 | 8.95 |

PHARMACOLOGICAL AND TOXICOLOGICAL TESTS

The most active compounds of formula (I) of the present invention were submitted to pharmacological tests to put in evidence their in vitro and in vivo cardioprotective effects, as well as their hemodynamic properties and toxicity.

The methods used were the following:

In vitro cardioprotective effect

Isolated guinea-pig ventricular myocytes were obtained following the method described by Powell et al. (*J. Physiol.,* 1980, 102: 131) as modified by Levi et al. (*J. Physiol.,* 1990, 425:9P). Cell hypercontracture and death was obtained either by incubation under $N_2$ atmosphere or by incubation with veratridine which induced important changes in the ionic homeostase of cardiomyocytes (Hiroko Hashizume et al., *European Journal of Pharmacology,* 1974, 271: 1–8). Results expressed as percentage of cells protected from hypercontracture i.e. maintaining its rod-shaped morphology with reference to vehicle-treated cells are given in the tables I and II hereafter.

In order to confirm the cardioprotection, the activity of one of the most interesting compound (example 31 according to the invention) was tested on guinea-pig ventricular cardiomyocytes action potential (AP) in the presence of veratridine or in anoxic condition. The action potential (AP) time courses of guinea-pig ventricular cardiomyocytes treated with veratridine or made anoxic by incubation under N2 atmosphere were measured (patch clamp technique) in absence and presence of the compound of example 31 according to the invention. This compound does not influence significantly the normal action potential but it prevents (100–300 nM) the prolongation of cardiomyocyte action potential duration induced by veratridine. In anoxic conditions, there is a shortening of cardiomyocyte action potential duration related mainly with an activation of K+-ATP dependent current. This effect is inhibited dose-dependently and strongly by the compound of example 31 according to the invention (100–300 nM).

TABLE I

Percentage of cells protected from hypercontracture obtained by incubation under N2 atmosphere:

| Compounds (30 nM) according to the examples: | % Protection |
|---|---|
| 12 | 80 |
| 22 | 63 |
| 23 | 50 |
| 24 | 60 |
| 25 | 50 |
| 31 | 58 |

TABLE II

Percentage of cells protected from hypercontracture obtained by incubation with veratridine:

| Compounds (1 µM) according to the examples: | % Protection |
|---|---|
| 12 | 57 |
| 22 | 37.5 |
| 23 | 41.3 |
| 24 | 37.5 |
| 25 | 34 |
| 31 | 64 |

In vivo cardioprotective effect

Cardiac death and arrhythmias were induced by the coronary occlusion and reperfusion method in anaesthetised rats according to the method of Seyle et al. (*Angiology,* 1960, 11, 398–407) modified by Krzeminski T.

("proceedings of 7$^{th}$ Freiburg Focus of Biomeasurement", Strasbourg, 16–19 September 1991) Cardiovascular and Respiratory in vivo Studies, Biomesstechnik, Verlag March GmbH, Germany) and according to the LAMBETH conventions (Walker M. J. A. et al., Cardiovasc Re., 1998, 22, 447–455). The products have been administered orally (one day and one hour before the experiment). Table III hereafter presents the results obtained. They are given in percentage of protection against the mortality and the arrhythmias (ventricular fibrillations).

TABLE III

Protective effect in vivo

| COMPOUND (2 × 20 mg/kg) ACCORDING TO EXAMPLE No: | % PROTECTION AGAINST DEATH | % PROTECTION AGAINST VENTRICULAR FIBRILLATIONS |
|---|---|---|
| 12 | 100 | 100 |
| 22 | 100 | 50 |
| 23 | 100 | 75 |
| 24 | 100 | 37.5 |
| 25 | 100 | 50 |
| 31 | 85.7 | 73.4 |

Hemodynamic effect

The most active compounds according to the invention have been tested in order to analyse their hemodynamic activity. In anaesthetised rat the intravenous administration of different dosages (30, 100, 300 and 1000 mg/kg) of the mentioned compounds did not influence significantly the following parameters: systolic, diastolic and mean arterial blood pressure, heart rate, ejection time, left ventricular systolic pressure, left ventricular end diastolic pressure dP/dt$_{max}$ and dPdt$_{min}$., contractility index and relaxation time.

Toxicity

The most active compounds according to the invention present a low per oral toxicity with LD50 more than 2000 mg/kg in the rat.

Conclusion

The pyridyl compounds of formula (i) according to the invention are able to protect the cardiomycytes against damages induced by ionic modifications (responsible for most of cardia pathology) and in such a way, they are able to protect the treated animals (rats) against death related to cardiac dysfunction and arrhythmia. Consequently, they are potentially cardioprotective agents in different human cardiac diseases (for example cardiomyopaties, myocardium infarction, angina, cardiac failures, coronary vasospasm, valvular heart disease, etc.). Moreover, they have a lower per oral toxicity and in therapeutic dosages, they do not present a deleterious hemodynamic activity.

What is claimed is:

1. A pyridyl compound of the formula.

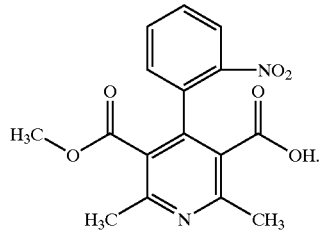

2. A pyridyl compound of the formula.

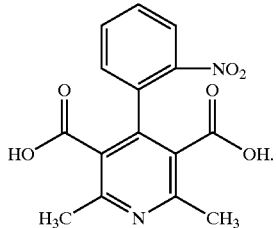

3. A composition comprising the compound according to claim 1, in combination with a pharmaceutical excipient.

4. The composition according to claim 3, wherein said excipient is selected from the group consisting of tablets, syrup and a sterile aqueous solution for injection.

5. A composition comprising the compound according to claim 2 in combination with a pharmaceutical excipient.

6. The composition according to claim 5, wherein said excipient is selected from the group consisting of tablets, syrup and a sterile aqueous solution for injection.

* * * * *